United States Patent [19]
Tuvim et al.

[11] Patent Number: 5,901,995
[45] Date of Patent: May 11, 1999

[54] DEVICE FOR COLLECTION OF CONTAMINATED OBJECTS

[76] Inventors: Yuri Tuvim; Mary-Louise Giuliano, both of 22 Jenison St., Newton, Mass. 02160

[21] Appl. No.: 09/084,326

[22] Filed: May 26, 1998

[51] Int. Cl.$^6$ ............................ A41D 19/00; A47L 13/18
[52] U.S. Cl. .................................. 294/25; 2/158; 294/1.3
[58] Field of Search ............................ 294/1.3, 25, 131; 2/16, 20, 158–160, 161.6–161.8; 15/104.8, 227; 119/161; 383/4, 7, 42, 70, 71, 77

[56] References Cited

U.S. PATENT DOCUMENTS 4,677,697  7/1987  Hayes ................................... 294/1.3 X
5,568,955  10/1996  Giuliano et al. ......................... 294/1.3

*Primary Examiner*—Johnny D. Cherry
*Attorney, Agent, or Firm*—Ilya Zborovsky

[57] ABSTRACT

A device for individual collection of contaminated objects has a substantially elongated element having a first hollow portion formed to receive a user's palm and provided with a projection for receiving a user's thumb, and a second portion extending from the first portion and having an inlet opening for insertion of the user's arm, the second portion having a width which is at least greater than a width of the first portion, so that when a user by manipulations with the first portion and the projection collects the objects, the second portion can be turned over the first portion and farther so that the element is turned inside out to produce a bag-like structure with contaminated objects inside, and a unit for closing the element after it has been converted inside out, the closing a unit being a strap formed as a rear part of the second portion which is formed of one piece with a remaining part of the second portion and includes a plurality of transverse and longitudinal cuts, the rear part in an inoperative position being coextensive with the second portion while in an operative position the strap being unfolded and forming an elongated element for tying up the device with both ends of the strap which are connected of one piece to the remaining part of the second portion.

5 Claims, 2 Drawing Sheets

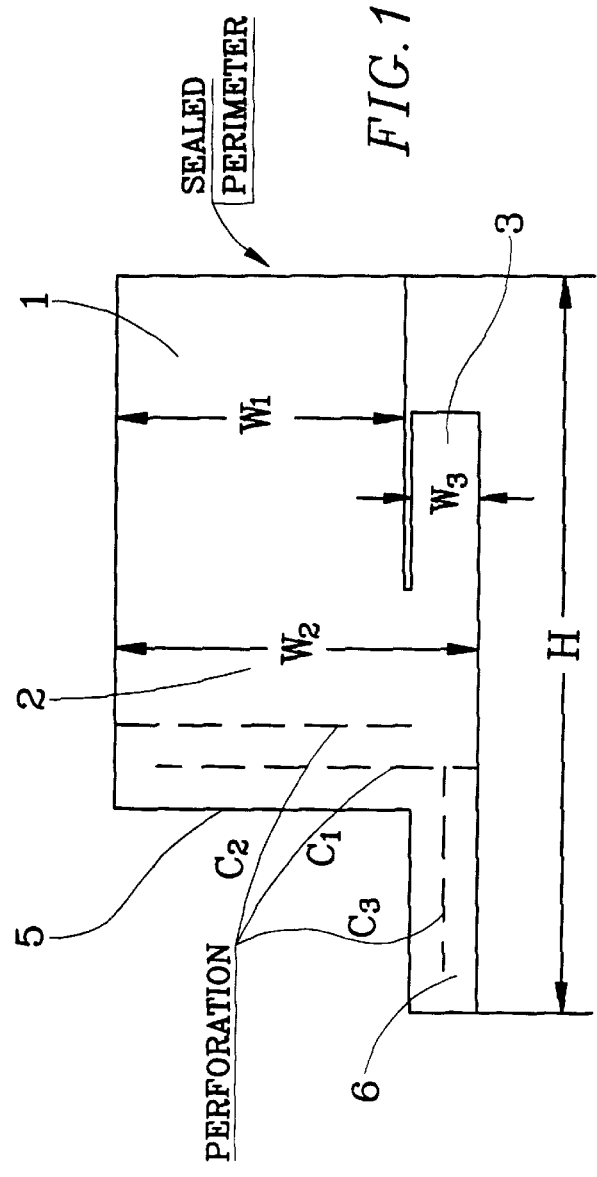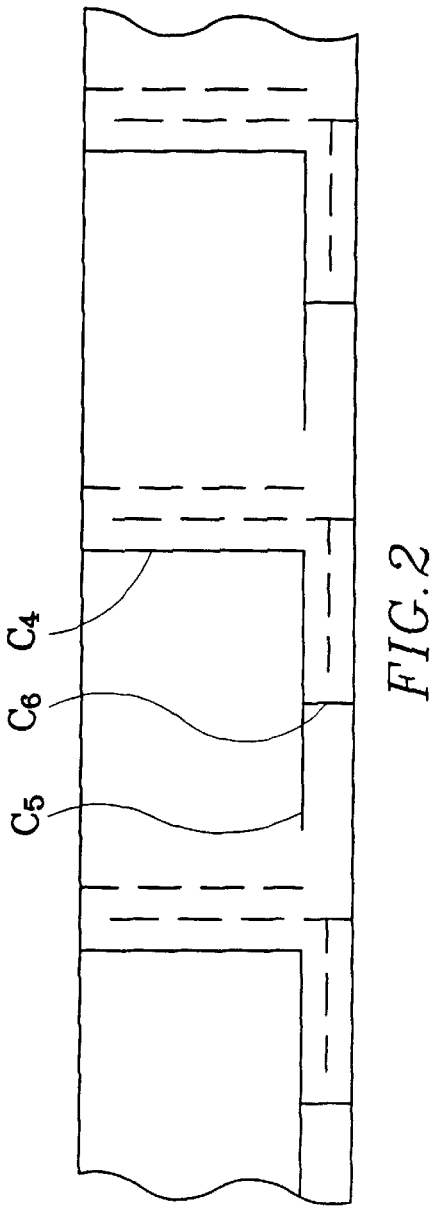

DEVICE FOR COLLECTION OF CONTAMINATED OBJECTS

BACKGROUND OF THE INVENTION

The present invention relates to a device for collection of contaminated objects.

The need for removing and/or collecting contaminated objects is evident in many areas of life: in hospitals, nursing homes, households and workplaces. A device which does the job can be also used by police to collect and store material evidence.

In our U.S. Pat. No. 5,568,955 we proposed a device which is formed as a one-piece integral plastic element. The device is easy to use, it is disposable, and inexpensive.

SUMMARY OF THE INVENTION

Accordingly, it is an objective of present invention to provide a device for individual collection of contaminated objects which is a further improvement of our device.

In keeping with these objectives and with others which will become apparent hereinafter, one feature of the present invention resides, briefly stated, in a device for individual collection of contaminated objects, comprising a substantially elongated element having a first hollow portion formed to receive a user's palm and provided with a projection for receiving a user's thumb, and a second portion extending from the first portion and having an inlet opening for insertion of the user's hand, wherein the second portion has a width which is at least equal to the sum of the width of the first portion and the width of the projection, so that when a user by manipulations with the first portion and a projection collects an object, the second portion can be turned over the first portion and farther so that the element is turned inside out to produce a bag-like structure with the object inside; and means for closing the element after it has been converted inside out, the closing means including a strap formed as a rear part of the second portion which is formed of one piece with a remaining part of the second portion and includes at least one transverse cut and at least one longitudinal cut, the rear part in an inoperative position being coextensive with the second portion while in an operative position the strap is unfolded and forms two elongated elements for tying up the device with both ends of the strap which are connected to the second portion.

In particular, since the cuts in the rear part of the second portion which eventually form a tying element include a transverse cut and a longitudinal cut, the material consumption of the device is reduced. Moreover, the successive arrangement of the devices makes it possible to produce them in one continuous strip in the most economical way.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 is a view showing a device for individual collection of contaminated objects in an initial position;

FIG. 2 is a view of a strip with a plurality of the produced devices;

DESCRIPTION OF PREFERRED EMBODIMENTS

Figure 3:
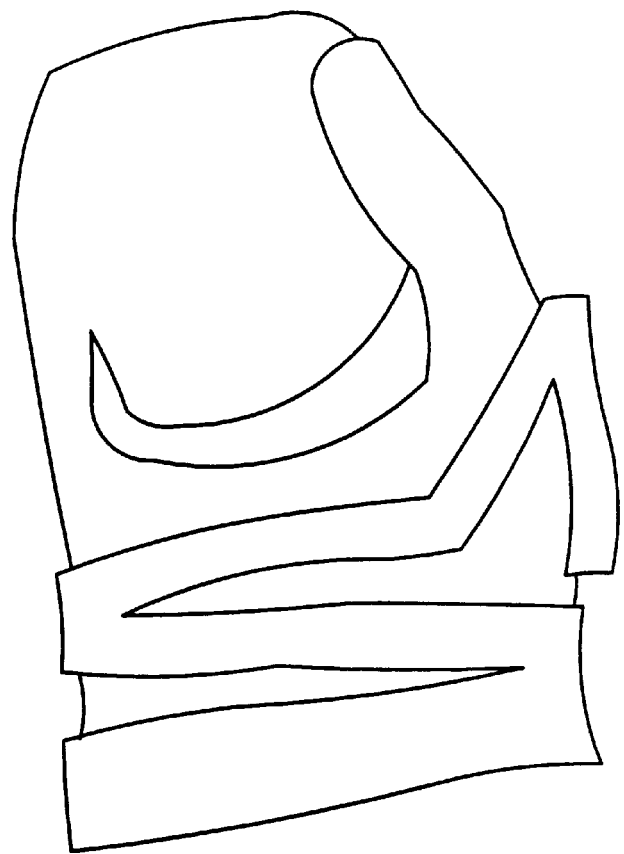
FIG. 3 is a view showing the device partly inverted during operation.

A device for individual collection contaminated objects in accordance with the present invention is identified as a whole with reference character H. It is formed as a flat hose-shaped elongated element which is composed of plastic, preferably of a biodegradable plastic. The element has a first hollow portion which is identified with reference numeral 1. The first hollow portion is closed at all sides with the exception of a rear side so that the user's palm can be introduced into the first portion and be completely accommodated there. A hollow projection 3 extends laterally parallel to the first portion 1 and can accommodate a user's thumb. The portions 1 and 3 serve for collecting objects from the ground and other places.

A second portion 2 extends rearwardly from the portion 1 and the projection 3 and is open at its rear end. The user can insert his arm into the device through a rear opening 5 and then push it all the way into the first portion 1 with the thumb inserted in the projection 3.

The device is further provided with means for closing the device after the objects have been collected and are accommodated in the device. The closing means include a meandering strap 6 formed at the rear part of the second portion 2 by at least two transverse perforations or cuts C1 and C2 and one longitudinal perforation C3. As can be seen from FIG. 2, the devices can be produced from a single elongated work piece formed as a hose by separating cuts. Each separating cut includes a transverse cut C4 and a longitudinal cut C5 separating the first portion of the device from the rear part of the second portion of the neighboring device and also forming a separation between the projection 3 and the first portion 1 of the device, and also a short transverse cut C6 separating the projecting of the device from the rest of the rear part of the second portion of the neighboring device.

In order to produce the device, it is cut from the flat hose-shaped workpiece along the cuts C4, C5, C6 and sealed along the edges of these cuts.

The device operates in the following manner.

Figure 4:
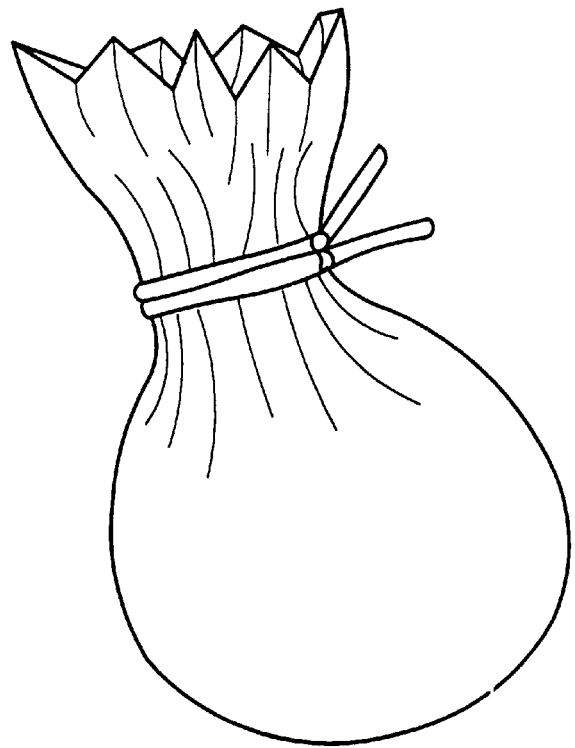
FIG. 4 is a view showing the inventive device in its final position with the collected object inside.

In order to collect an object the user puts his palm into the device with his fingers inserted into the first portion 1 and his thumb inserted into the projection 3. The object, for example, is located on the ground, and the user puts his arm with the device on it on top of the object. Then by manipulations of the palm with the portion 1 and the projection 3, he scoops the object from the ground and holds it. Thereafter, with a second hand, he turns the second portion 2 onto the first portion 1 as shown in FIG. 3 and, finally, (FIG. 4) the device is turned inside out and the object is located inside the device. Then the strap 6 is tied around a part of the portion 2, and a closed bag with the object inside is therefore produced. Since the device is composed of an inexpensive polymeric material and since the material is biodegradable, the device can be immediately discarded.

It will be understood that each of the elements described above, or two or more together, may also find a useful application in other types of constructions differing from the types described above.

While the invention has been illustrated and described as embodied in device for individual collection of contaminated objects it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A device for individual collection of contaminated objects, comprising a substantially elongated element having a first hollow portion formed to receive a user's palm and provided with a projection for receiving a user's thumb, and a second portion extending from said first portion and having an inlet opening for insertion of the user's arm, said second portion having a width which is at least equal to a width of said first portion, so that when a user by manipulations with the first portion and the projection collects contaminated objects, the second portion can be turned over the first portion and farther so that said element is turned inside out to produce a bag-like structure with contaminated objects inside; and means for closing said element after it has been converted inside out, said closing means being a strap formed as a rear part of said second portion which is formed of one piece with a remaining part of said second portion and includes exclusively transverse and longitudinal cuts to reduce a material consumption of the device and to allow a successive arrangement of the devices to produce them from one continuous strip substantially without waste of a material, said rear part in an inoperative position being coextensive with said second portion while in an operative position said strap being unfolded and forming an elongated element for tying up the device with both ends of said strap which are connected of one piece to the remaining part of said second portion.

2. A device as defined in claim 1, wherein said element is composed of a biodegradable plastic.

3. A device as defined in claim 1, wherein said strap and said first and second portions together are formed of one piece with one another so that said element is a one-piece element.

4. A device as defined in claim 1, wherein said cuts include at least one transverse cut and at least one longitudinal cut.

5. A device as defined in claim 1, wherein said cuts include two said transverse cuts.

* * * * *